(12) United States Patent
Backhaus et al.

(10) Patent No.: US 8,807,402 B2
(45) Date of Patent: Aug. 19, 2014

(54) DISPOSABLE GLOVE AND APPARATUS FOR APPLYING A GLOVE TO A USER'S HAND

(76) Inventors: Benjamin Stephan Backhaus, Mount Isa (AU); Stephan Backhaus, Berowra (AU); Paul Stanley, Hampton Park (AU)

( * ) Notice: Subject to any disclaimer, the term of this patent is extended or adjusted under 35 U.S.C. 154(b) by 1183 days.

(21) Appl. No.: 13/119,614

(22) PCT Filed: Sep. 17, 2008

(86) PCT No.: PCT/AU2008/001377
§ 371 (c)(1),
(2), (4) Date: Aug. 10, 2011

(87) PCT Pub. No.: WO2009/036499
PCT Pub. Date: Mar. 26, 2009

(65) Prior Publication Data
US 2011/0283439 A1    Nov. 24, 2011

(30) Foreign Application Priority Data
Sep. 17, 2007   (AU) ................................ 2007905066

(51) Int. Cl.
*A47G 25/80*  (2006.01)
*A47G 25/90*  (2006.01)
*A61B 19/04*  (2006.01)

(52) U.S. Cl.
CPC ............ *A47G 25/904* (2013.01); *A61B 19/045* (2013.01); *A61B 2019/046* (2013.01)
USPC ....................................................... 223/111

(58) Field of Classification Search
CPC . A47G 25/90; A47G 25/904; A41D 19/0055; A41D 19/0068; A41D 19/0072; A61B 19/045; A61B 2019/046

USPC ........................................................... 223/111
See application file for complete search history.

(56) References Cited

U.S. PATENT DOCUMENTS

| | | | |
|---|---|---|---|
| 4,034,853 A | 7/1977 | Smith | |
| 4,094,120 A | 6/1978 | Goncalves | |
| 4,677,697 A | 7/1987 | Hayes | |
| 4,773,532 A * | 9/1988 | Stephenson | 206/278 |
| 4,909,413 A | 3/1990 | McCutcheon | |
| 4,915,272 A * | 4/1990 | Vlock | 223/111 |
| 6,053,380 A * | 4/2000 | Sherrod | 223/111 |
| 6,375,034 B1 * | 4/2002 | Corbett | 221/46 |
| 6,435,388 B1 * | 8/2002 | Binder et al. | 223/111 |

(Continued)

FOREIGN PATENT DOCUMENTS

| | | |
|---|---|---|
| CN | 2228143 A | 5/1996 |
| CN | 1441653 A | 5/2001 |

(Continued)

*Primary Examiner* — Nathan Durham
(74) *Attorney, Agent, or Firm* — Pearne & Gordon LLP

(57) ABSTRACT

The present invention relates to a package of disposable gloves and to a method and an apparatus which can use the package to enable the gloves to be applied to a user's hands. The gloves are stored in a roll and are unrolled and opened by the apparatus so that a user can hygienically insert their hand into a glove without touching the glove. The user, with their hand in the glove can then sever the glove from the roll of gloves by moving their hand downwardly and away from the apparatus. The apparatus can then unroll and open another glove for the user to insert their other hand.

26 Claims, 13 Drawing Sheets

(56) References Cited

U.S. PATENT DOCUMENTS

| | | | |
|---|---|---|---|
| 6,832,708 B2 * | 12/2004 | Sinai | 223/111 |
| 6,932,253 B2 * | 8/2005 | Sato | 223/111 |
| 7,377,410 B1 * | 5/2008 | Webb | 223/111 |
| 7,509,792 B2 | 3/2009 | Furlotti | |
| 7,635,067 B1 * | 12/2009 | Flynn | 223/111 |
| 7,805,772 B2 * | 10/2010 | Williams | 2/111 |
| 2003/0094468 A1 * | 5/2003 | Sinai | 223/111 |
| 2004/0149788 A1 | 8/2004 | Sato | |
| 2006/0010563 A1 | 1/2006 | Michel et al. | |
| 2006/0144878 A1 * | 7/2006 | Williams | 223/111 |
| 2006/0200891 A1 | 9/2006 | Geraci | |
| 2007/0170213 A1 * | 7/2007 | Gaines et al. | 223/111 |
| 2007/0227103 A1 | 10/2007 | Furlotti | |

FOREIGN PATENT DOCUMENTS

| | | |
|---|---|---|
| CN | 1964892 A | 5/2007 |
| DE | 3128547 A1 | 2/1983 |
| EP | 0 542 332 A2 | 5/1993 |
| FR | 2 638 068 A1 | 4/1990 |
| GB | 2 226 488 A | 7/1990 |
| JP | H06047320 D | 6/1994 |
| JP | 2004229872 A | 8/2004 |
| WO | 0189406 | 11/2001 |

* cited by examiner

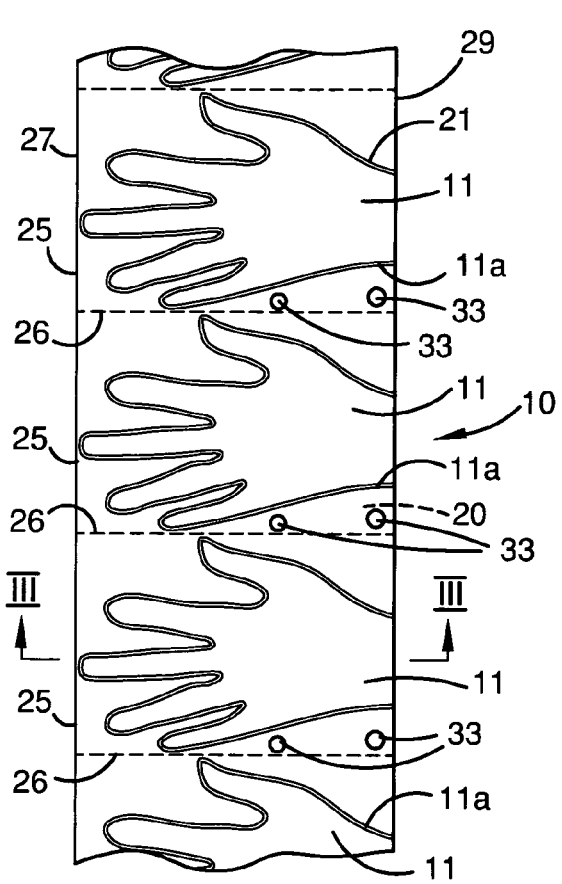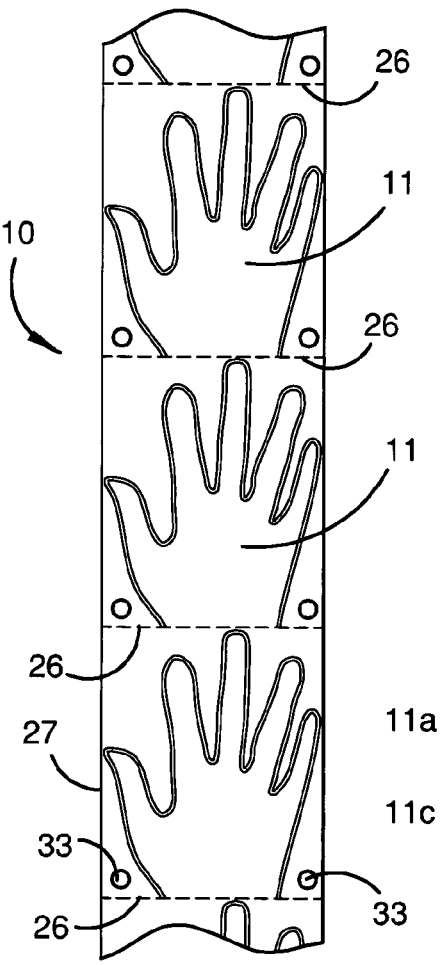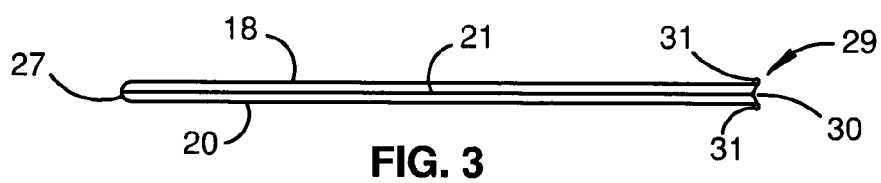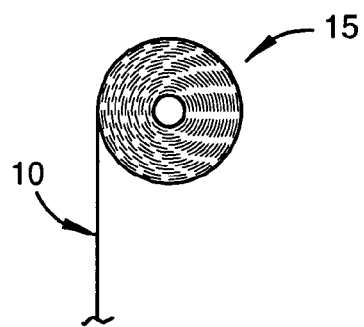

DISPOSABLE GLOVE AND APPARATUS FOR APPLYING A GLOVE TO A USER'S HAND

FIELD OF THE INVENTION

This invention relates to a package of disposable gloves and to a method and an apparatus which can use the package to enable the gloves to be applied to a user's hands.

BACKGROUND OF THE INVENTION

The use of disposable gloves is becoming common in a number of industries such as food handling establishments where food such as sandwiches or the like may be made and sold to a customer, or other open food products such as meats and the like are selected from a tray and wrapped for a customer to purchase. The use of such gloves is intended to improve hygiene and prevent the spread of germs which may take place if such food products are handled by the bare hands.

Conventionally, when such gloves are used they are merely selected from a box and are applied by the user to the user's hands. This requires the user to have significant contact with the gloves prior to, and during, application of the gloves to the user's hands which means that the outer surface of the gloves can become contaminated with any other germs or other unwanted material already on the user's hands.

SUMMARY OF THE INVENTION

The object of the present invention is to provide a package of disposable gloves which may be used with a method and an apparatus to more hygienically apply the gloves to a user's hands, and to such a method and an apparatus.

The invention in a first aspect may be said to reside in a package of disposable gloves, comprising:
 a plurality of gloves connected to one another in a line by a frangible connection which is breakable to separate one glove from the line;
 a glove edge transverse to the frangible connection to form an open cuff of each glove; and
 wherein each glove is formed from two layers which are joined together by a join to define the glove.

Preferably the gloves are formed in glove panels with each panel being connected to an adjacent panel by the frangible connection, the join comprising a heat seal in each panel defining the shape of the glove.

In one embodiment each panel is a rectangular panel and has webs outwardly of the join.

In one embodiment the glove has defined fingers and cuts are formed through the webs between the fingers to separate the fingers.

However, in other embodiments the webs between the fingers may be left intact.

In another embodiment the glove has fingers and the join of the glove which defines the fingers forms the periphery of the panel at the fingers.

Thus, in this embodiment no web is formed between the fingers of each glove.

In other embodiments the glove may be a mitten without defined fingers.

Preferably the package of disposable gloves is in the form of a roll of gloves.

This aspect of the invention may also be said to reside in a package of disposable gloves for use with a glove applying machine for enabling the gloves to be applied to a user's hands, comprising:
 a plurality of gloves connected to one another in a line by a frangible connection which is breakable to separate one glove from the line;
 each glove being formed from two layers which are joined together by a join to define the glove; and
 locating indicia for allowing the gloves to be registered in the apparatus.

In one embodiment the locating indicia comprises a marking.

In another embodiment the locating indicia comprises a hole.

In one embodiment of the invention at least one pin for location in the hole to register the package of gloves in the apparatus when a new package of gloves is loaded into the apparatus, to enable the gloves to be indexed through the apparatus.

Preferably the gloves are formed in glove panels with each panel being joined to an adjacent panel by the frangible connection, the join comprising a heat seal in each panel defining the shape of the glove.

Preferably each panel has a web portion outwardly of the join and the locating indicia is located on the web portion.

According to one embodiment, preferably an open cuff of each glove is formed at the edge of each panel that is transverse to the frangible connection. In other words, the glove is oriented horizontally or "East to West" relative to the line.

According to an alternative embodiment, preferably an open cuff of each glove is formed at an edge of the panel at the frangible connection between the panels. In other words, the glove is oriented vertically or "North to South" relative to the line.

In the most preferred embodiment the marking indicia comprises two holes in each panel.

Preferably the frangible connection comprises a perforated line.

However, in other embodiments the frangible connection could comprise small attaching strips between each glove, the attaching strips being breakable when one glove is pulled away from an adjacent glove in the line of gloves.

Preferably the package of disposable gloves comprises a roll of gloves.

The invention in a second aspect may be said to reside in a method of hygienically locating a glove on a user's hand, comprising:
 mechanically locating the glove at a hand insertion location;
 opening the glove; and
 inserting a hand in the glove.

Preferably the glove is opened at the hand insertion location.

Preferably the glove is supplied as one glove in a line of gloves joined by a frangible connection, so that the glove when the user's hand is located in the glove is torn from the line by movement of the user's hand and the glove.

Preferably the glove has an open cuff and a finger portion and the glove is located in an orientation such that a line between the cuff of the glove and the end of the finger portion of the glove is substantially horizontal.

Preferably the glove has a first layer defining the back of the glove and a second layer defining the palm of the glove, and the glove is open by moving the first and second layers apart to enable a person to insert his/her hand through the cuff into the glove.

Most preferably both the first and second layers are moved. However, in other embodiments only one of the layers could be moved whilst the other is substantially stationery.

The invention may also be said to reside in an apparatus for enabling hygienic location of a glove on a hand, comprising:
- a storage for storing a package of disposable gloves;
- an indexing device for moving the gloves from the storage to a hand insertion station; and
- a glove opening device for opening a glove so a user can insert his or her hand into the glove at the hand insertion station.

In one embodiment of the invention the storage is a compartment for storing a roll of gloves comprising a continuous line of gloves with the gloves being joined to one another by a frangible connection in the line.

Preferably, the indexing device comprises a movable gripping device for movement between the hand insertion station and a line gripping station so that the device can move relative to the line between the insertion station and the gripping station, and can grip the line at the gripping station so the line is drawn with the device upon return movement from the gripping station to the hand insertion station.

Preferably the gloves in the line have a first layer and a second layer and the glove opening device comprises a gripper for gripping at least one of the layers, and a gripper moving element for moving the gripper and the at least one of the layers relative to the other layer to open the glove.

Preferably the glove is gripped and opened during movement of the gripper device between the gripping station and the hand insertion station.

According to one embodiment, the gripper comprises a block of material through which air can flow, and the gripper mover element comprises a bladder, wherein upon inflation of the bladder the material is forced against at least one of the layers, and when vacuum is applied to the material air flows through the material to hold the layer against the material, and upon deflation of the bladder the material and the layer are drawn away from the other layer to thereby open the glove.

Preferably the material comprises a open cell foam material.

Preferably the bladder has a spring element for controlling inflation and deflation of the bladder to firstly move the material against the layer upon inflation of the bladder, and draw the material and the layer away from the other layer upon deflation of the bladder.

According to an alternative embodiment, the gripper comprises an inflatable assembly and a sealing formation having one or more than one suction points, wherein upon inflation of the inflatable assembly, at least one of the suctions points of the sealing formation is located against at least one of the layers, and upon deflation of the inflatable assembly, the layer is drawn away from the other layer to thereby open the glove.

Preferably, the inflatable assembly comprises a bellows.

Preferably, the rate of inflation or deflation of the inflatable assembly is controlled by a piston and cylinder that supplies air into, or draws air from, the inflatable assembly, and suction of the suctions points is controlled by a separate piston and cylinder.

Preferably, the or each piston and cylinder assembly is operable by a linear actuator controlled by a solenoid.

Preferably the indexing device further comprises a pair of rollers, a gear attached to each roller the gears meshing together so the rollers are able to rotate in unison but in opposite directions, the rollers having a groove and rib so that when the groove of one roller engages with the rib of the other roller the line is gripped between the rollers, and so that upon movement of the indexing device from the gripping station to the hand insertion station the line is drawn off the package, and upon movement of the indexing device from the hand insertion station to the gripping station the rollers rotate relative to the line during movement of the indexing device until the groove and rib re-engage to thereby grip the line between the rollers.

In one embodiment a driver is provided to rotate the rollers only during movement of the gripping device from the hand insertion station to the gripping station.

In one embodiment the driver comprises a motor may be provided for facilitating rotation of the rollers during movement of the indexing device from the hand insertion station to the gripping station.

The motor may have a clutch to prevent rotation of the rollers during movement of the indexing device from the gripping station to the hand insertion station.

In another embodiment the driver comprises a rack and gear assembly, with the gear coupled to one of the rollers and the rack fixed and engaging the gear so that when the indexing device is moved from the hand insertion station to the gripping station engagement of the gear and the rack causes rotation of the gear and therefore rotation of the rollers.

In this embodiment the gear also synchronises rotation of the rollers with movement of the indexing device between the hand insertion station and the gripping station.

Preferably a sensor is provided for sensing the insertion of a user's hand into the glove at the hand insertion station, and then removal of the glove from the line at the hand insertion station, to thereby activate the indexing device to cause the indexing device to move from the hand insertion station, to the gripping station, and back to the hand insertion station so a new glove is open at the hand insertion station ready for insertion of a user's hand.

Preferably the apparatus includes locating elements for engaging the line when a new package is located in the apparatus to correctly register the line in the apparatus.

Preferably the line has holes and the locating elements comprise pins for passing through the holes when the package is loaded into the apparatus, and for withdrawal from the holes after the package is loaded in the apparatus.

Preferably the pins are driven between a locating position where they can pass through the holes and a retracted position away from the line, by opening and closing movement of a door of the apparatus to provide access to the storage of the apparatus.

Preferably at least one of the rollers is spring biased into engagement with the other of the rollers so that the rollers can be slightly separated to facilitate location of the line between the rollers during loading of a package into the apparatus.

This aspect of the invention may also be said to reside in an apparatus for enabling hygienic location of a glove on a hand, comprising:
- a housing having a front opening and a bottom opening which provide access to a hand insertion station;
- a storage for storing a package of disposable gloves, so the gloves are presented at the hand insertion station in an orientation so that a line between a cuff portion of the gloves and a fingertip portion of the gloves is substantially horizontal, and with the cuff portion of the gloves facing the front opening;
- a glove indexing device for moving a glove from the storage to the hand insertion station so a user can insert his or her hand into the glove through the cuff portion; and
- wherein to locate the glove on the hand and remove the glove from the apparatus, a user inserts his or hand through the front opening into the glove and then moves his or her hand with the glove on his or her hand downwardly through the bottom opening.

This aspect of the invention may also be said to reside in an apparatus for enabling hygienic location of the glove on a hand, comprising:

a storage for storing a package of disposable gloves;

an indexing device for moving the gloves from the storage to a hand insertion station; and a glove opening device comprising at least one block of material through which air can flow, an inflatable bladder, and at least one air supply and vacuum system for supplying air to the bladder to inflate the bladder to move the block to a position adjacent the glove, for drawing a vacuum through the block so a portion of the glove is drawn against the block, and for deflating the bladder so the block moves with the bladder to move a portion of the glove away from another portion of the glove to open the glove to enable a user to insert his or hand into the glove at the hand insertion station.

BRIEF DESCRIPTION OF THE DRAWINGS

Preferred embodiments of the invention will be described, by way of example, with reference to the accompanying drawings in which:

FIG. 1 is a view of a line of gloves formed as a package according to one embodiment;

FIG. 2 is a view similar to FIG. 1 of a second embodiment;

FIG. 3 is a view along the line of FIG. 1;

FIG. 4 is a side view of the package of gloves in the form of a roll of gloves;

DETAILED DESCRIPTION OF THE PREFERRED EMBODIMENTS

Figure 5:
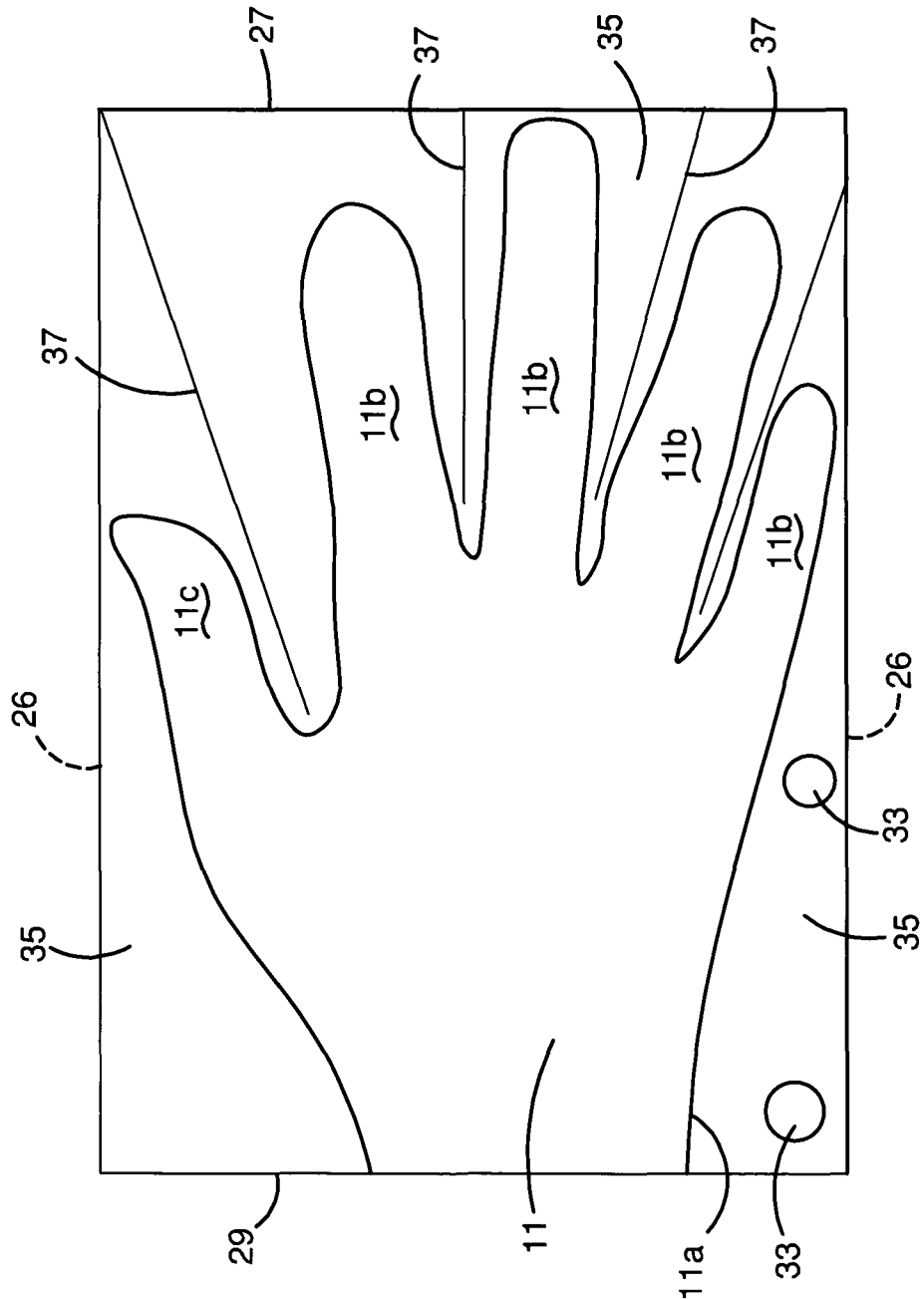
FIG. 5 is a more detailed view of one glove in the line of FIG. 1.

With reference to FIG. 1 a line of gloves 10 is shown which form a package of gloves such as a roll 15 as shown in FIG. 4. In other embodiments the package could comprise a zigzag layering of the line of gloves or any other compact packaging of the gloves.

The line of gloves 10 is formed from a first layer 18 and a second layer 20 (see FIG. 3). Each glove 11 in the line of gloves 10 is defined by a heat seal join 21 which defines the periphery of the glove (in other words the shape of the glove). Thus, the join heat seals the two layers 18 to 20 together along the outline 11a of the gloves to thereby define the shape of the gloves.

In the embodiment of FIG. 1, the gloves are formed in glove panels 25 formed by the two layers 18 and 20 and the glove panels 25 are defined by a frangible connection 26. The frangible connection 26 preferably comprises a perforated line so that one glove can be easily torn from the line 10 as will be described in more detail hereinafter.

In the embodiment of FIG. 1 the glove panels 25 have opposite edges 27 and 29 which are not connected to one another except where the join 21 intersects or contacts the edges 27 and 29. This therefore defines an open cuff 30 of each glove as is best shown in FIG. 3. The edge 29 may be beaded so that the open cuff of each glove 11 has a bead 31 to slightly strengthen that part of the glove and make it easy for a person to insert his or her hand into the glove.

Each panel 25 is also provided with two holes 33 which form locating indicia to facilitate location of the gloves in a glove applying apparatus to be described hereinafter.

FIG. 2 shows a second embodiment in which the gloves are configured in an "north-south" configuration rather than the "east-west" configuration of FIG. 1. Like reference numerals indicate like paths to those previously described.

In this embodiment the open cut of the glove will be formed when the perforated line 26 is torn during the separation of one glove 11 from the line of gloves 10.

FIG. 5 is a more detailed view of one glove 11 formed in a panel 26 of the type shown in FIG. 1.

As will be apparent from both FIG. 1 and FIG. 5 webs 35 are left outwardly of the join 11a, formed from the layers 18 and 20 of each panel 25.

If desired, cuts 37 can be made in the webs 35 between the fingers 11b of the gloves to separate the fingers. However, in other embodiments the webs can remain intact because they will be relatively thin and will still allow sufficient degree of relative movement of the fingers form most applications.

A cut 37 is also provided between the thumb 11c of the glove 11 and the index finger 11b adjacent the thumb 11c.

Since the disposable glove is usually only used for a very small amount of time, perhaps in the order of only 30 seconds or less, the webs will not interfere with movement of the hand or the work the person wearing the gloves is required to do.

Figure 6:
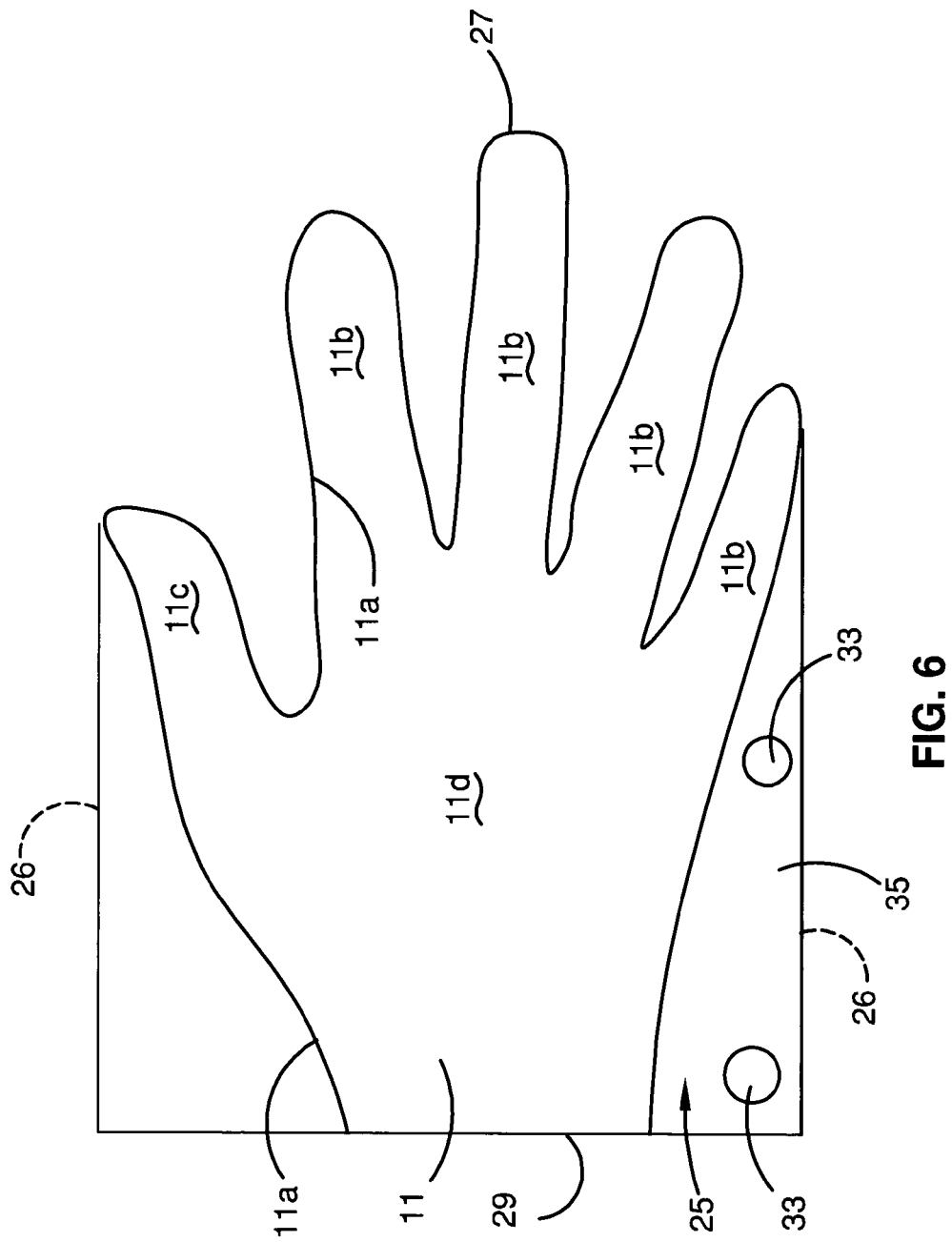
FIG. 6 is a more detailed view of one glove of the type shown in FIG. 1 in a modified form.

In still further embodiments of the invention the panels 25 may be of the type shown in FIG. 6 in which the panel is cut about the join 11a defining the fingers 11b so that no webs are provided between the fingers 11b and the thumb 11c. Webs 35 remain outwardly of the palm portion 11d of the hand.

In this embodiment the edge 27 is defined by the shape of the fingers as shown in FIG. 6.

In the embodiment of FIG. 6 the perforated line 26 extends from the edge 29 to the tip of the thumb 11c and between the edge 29 and the tip of the small finger 11b.

Figure 7:
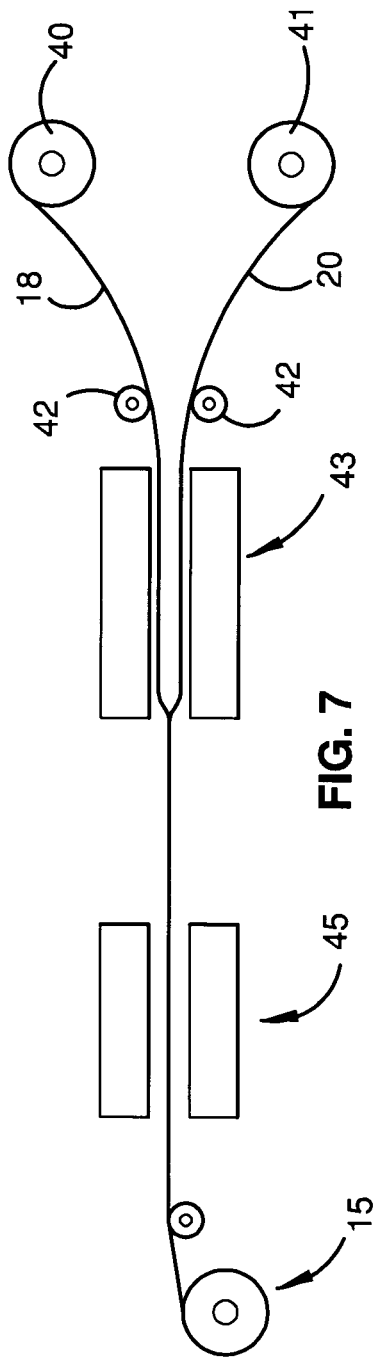
FIG. 7 is a side view of a machine for forming the package of gloves.
Figure 8:
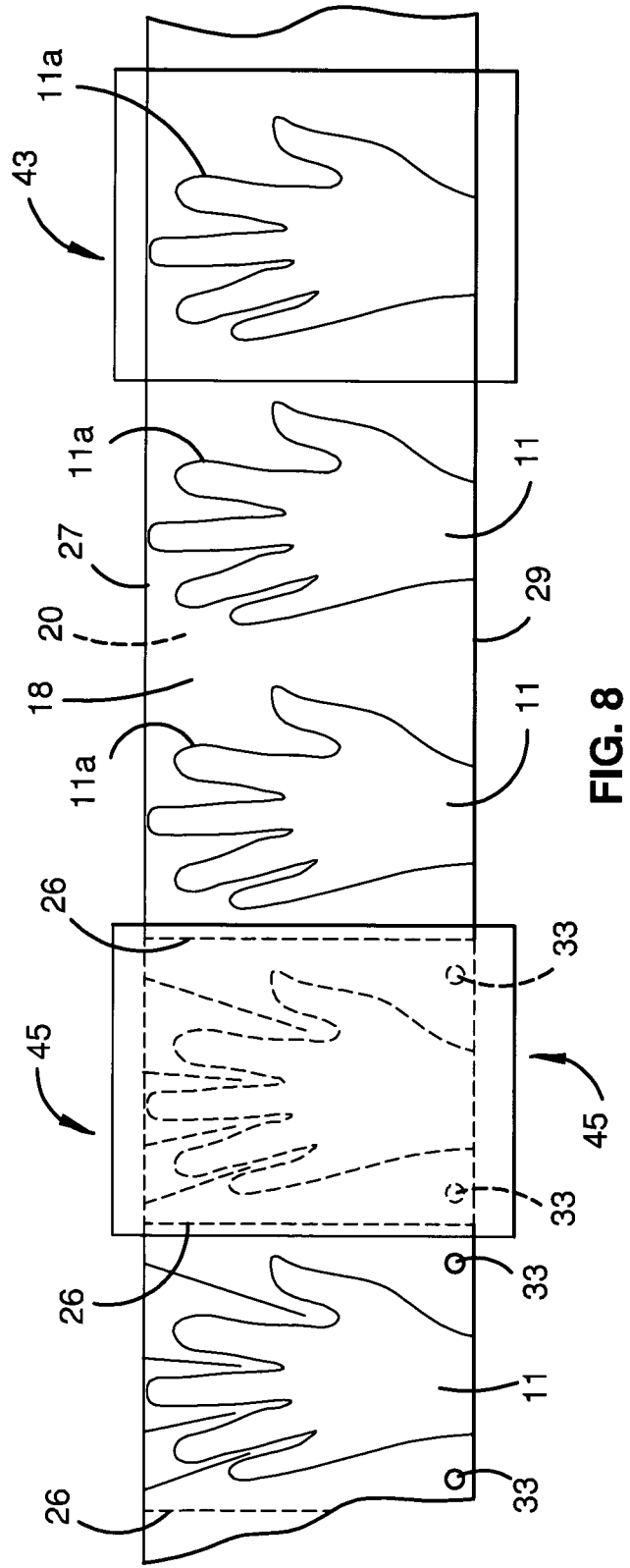
FIG. 8 is a top view of the machine of FIG. 7.

FIGS. 7 and 8 show, schematically, an example of how the package of gloves is formed.

Layers 18 and 20 are supplied from supply rolls 40 and 41 of the layer material and guided around one or more sets of idler rollers 42 to a heat sealing station 43. At the heat sealing station 43 the join 21 defining the periphery of the glove 11a is formed by applying heat along the line 11a via appropriate parts of the station 43 to heat weld the layers 18 and 20 together along the line 11a which defines the shape of the glove. Thus, the layers 18 and 20 are joined at the line 11a.

The layers 18 are then indexed to a cutting and perforating station 45 where the perforated line 26 is formed and also the holes 33 and cuts 37, the formed line of gloves 10 is then rolled onto a roll to form the package of gloves 15 shown in FIG. 4.

It should be understood that the apparatus shown in FIGS. 7 and 8 is schematic and merely illustrative and not intended to show all componentry of the machine performing the package of gloves. In any event, it will be appreciated that the compoenentry not shown in detail in FIG. 7 may readily be constituted by a combination of commercially available components.

FIGS. 9 to 14, and 16 and 17 show parts of an apparatus according to one embodiment of the invention. FIG. 15 shows a schematic illustration of the assembled apparatus comprising the parts shown in FIGS. 9 to 14, and 16 and 17 for hygienically applying the glove to a user's hand.

Figure 9:
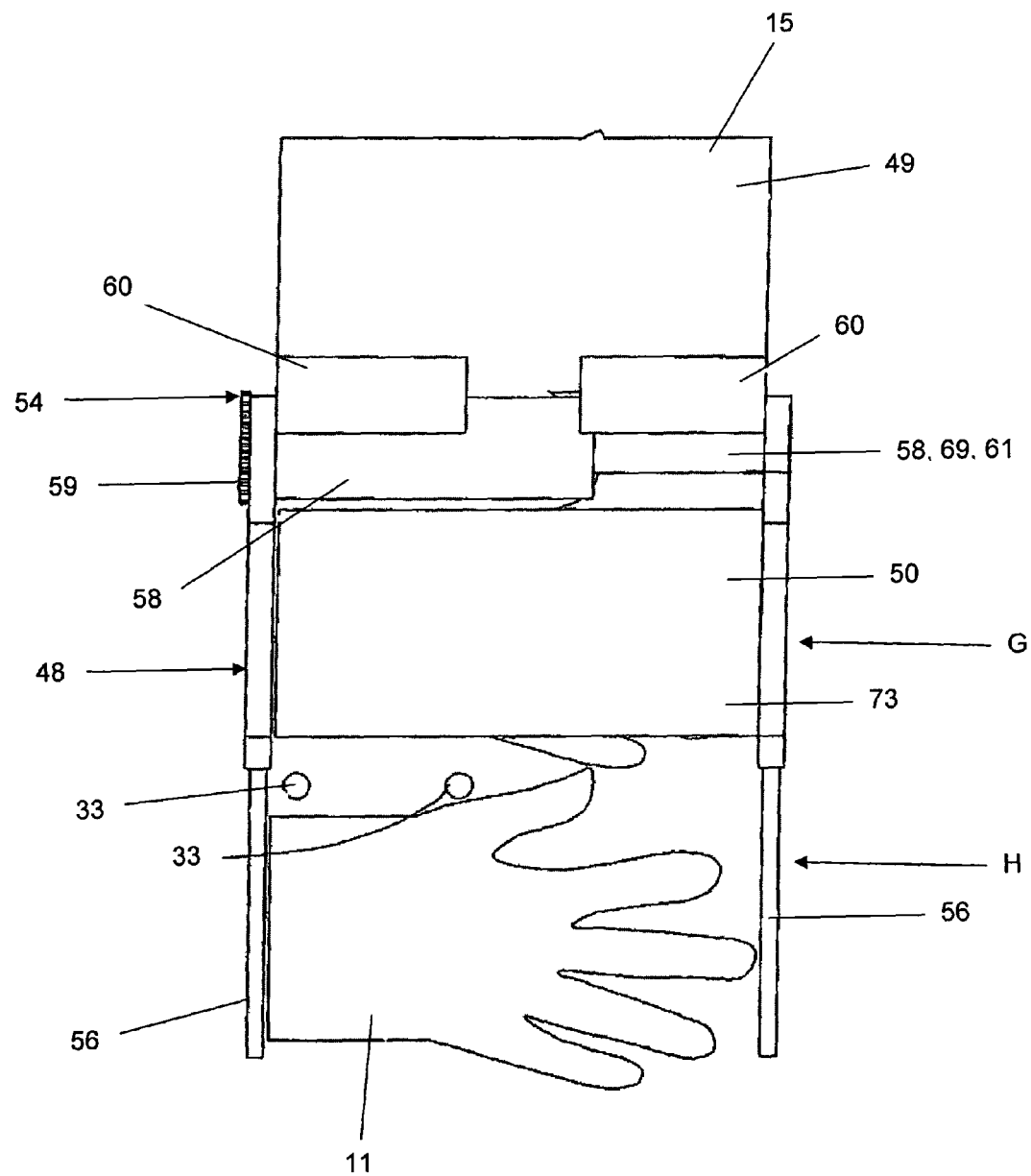
FIG. 9 is a side view of an apparatus according to one embodiment of the invention.
Figure 10:
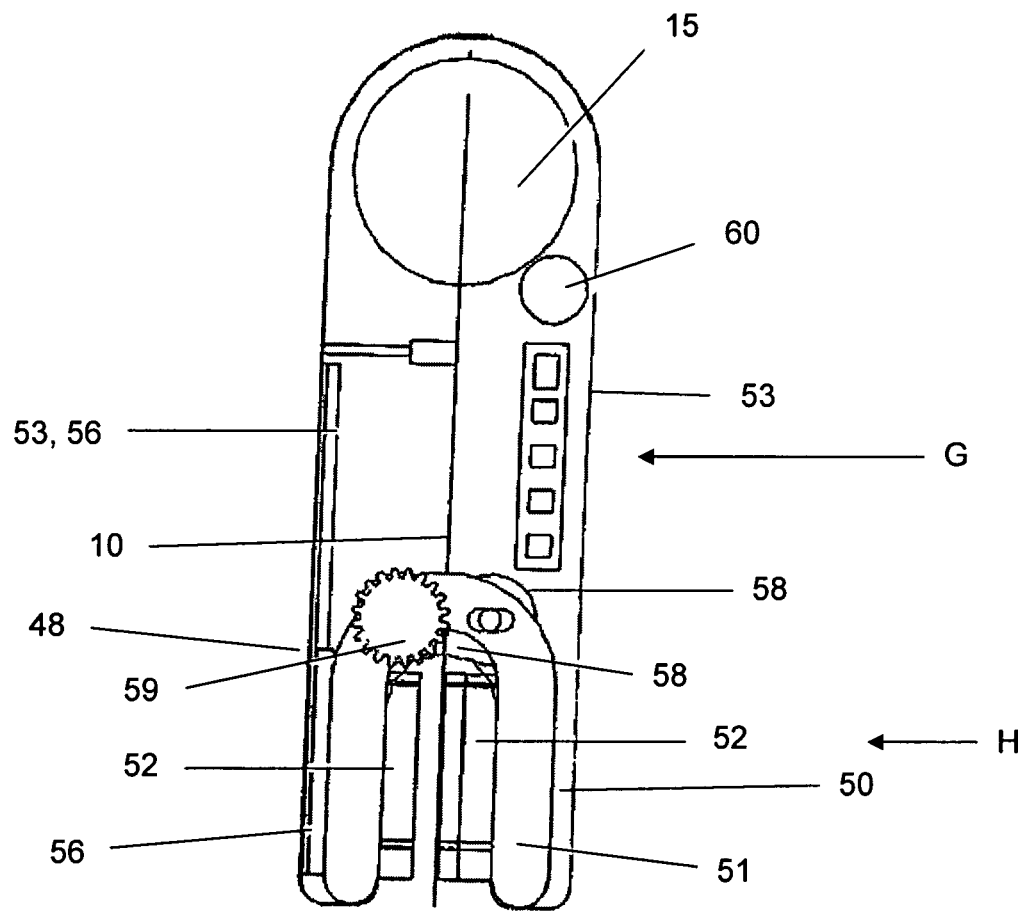
FIG. 10 is a front view of the apparatus of FIG. 9.
Figure 11:
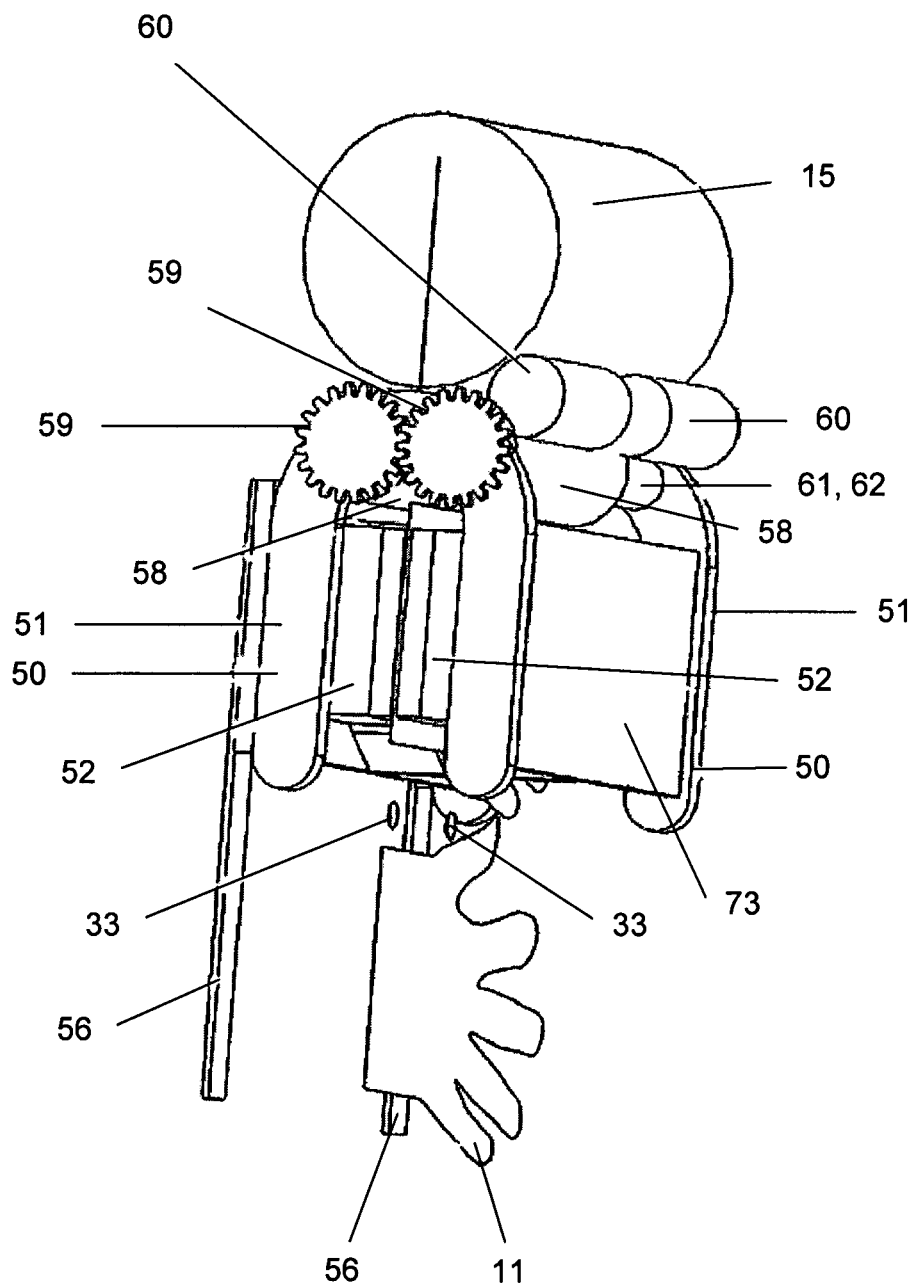
FIG. 11 is a perspective view of the apparatus of FIG. 9.

With reference to FIGS. 9, 10 and 11, the apparatus has a glove line 10 indexing device 48 comprising a support frame 50 which supports a pair of glove opening devices 52. Roll 15 of the gloves 11 is supported on a shaft (not shown) in a storage 49 and the line of gloves 10 is guided from the roll 15 through the devices 52 as is best shown in FIG. 10 and FIG. 11.

The frame 50 comprises two U-shaped frame members 51 which are supported on tracks 53 which, in turn, are supported by outer housing 55 (see FIG. 15).

The frame 50 is also connected to a pair of linear bearings 56 for moving the frame 50 vertically on guide tracks 53 as will be explained in more detail hereinafter.

The frame 50 also supports a line gripper 54 to gripping the line 10. The line gripper 54 comprises a pair of rollers 58 between which the line 10 of gloves 11 is guided. The rollers 58 have gears 59 at one end and the gears 59 are meshed to synchronise rotation of the rollers 58 so that they rotate in unison with one another but in opposite directions.

The outer housing 55 also supports two pressure pumps 60 for driving the devices 52 as will also be explained in more detail hereinafter.

An encoder 61 is provided on shaft 62 on which one of the rollers 58 is mounted for monitoring rotation of the rollers 58.

Movement of the frame 50 and the rollers 59 and associated operation of the devices 52 is as follows.

FIGS. 9 and 10 show the frame 50 in a raised upper gripping position at gripper station G in which the line of gloves 10 is gripped by the rollers 59 and extends between the devices 52. The linear bearing 56 moves the frame and rollers 59 downwardly to the hand insertion station H shown in FIG. 11 thereby pulling the line of gloves 10 downwardly with the frame 50 off the roll 15.

During downward movement of the frame 50 pressure is supplied to the devices 52 to cause the devices 52 to grip one of the gloves 11 on the line 10. After the glove has been gripped vacuum is then applied to the devices 52 to cause the devices 52 to separate thereby pulling the two layers 18 and 20 which make up the glove 11 away from one another to open the glove. At the same time as the vacuum is applied the pressure previously supplied to the devices 52 to cause gripping of the glove is released.

The glove is therefore held open with the frame 50 in the lower position at hand insertion station H shown in FIG. 11 so that a user can then insert his hand through front opening 62 of the housing 55 into the glove and the user simply draws his or her hand downwardly through the open bottom 64 of the housing 55 to tear the glove from the line 10 along the perforation 26 above the glove 11. Thus, the user's hand is removed from the apparatus with the glove on place without the user having to touch the outside of the glove.

As is best shown in FIGS. 9 and 15 a light emitting array 66 is provided on the frame 50 opposite a linear array of photo detectors 68. Light emitted by the emitters 66 is detected by the detectors 68 so that when a person's hand is located in the glove the light is blocked thereby providing an indication that a person's hand is in the apparatus and when the person tears the glove 11 from the line 10 by the downward movement of the hand previously mentioned, light is again detected by the array of photo detectors 68. Thus, this provides a signal indicative of the fact that a user has inserted his or her hand into the apparatus and removed his or her hand with a glove on it. This signal is used to activate the linear bearings 56 to again drive the frame 50 upwardly. As the frame 50 is driven upwardly the friction between the line 10 and the rollers 58 causes the rollers 58 to rotate thereby rolling up relative to the station line 10 of gloves 11. When the rollers 58 have rotated one full revolution as detected by the encoder 61a signal is supplied to shut off the linear bearings 56 to prevent further upward movement of the frame 50 indicative of the fact that the frame 50 has returned to its starting station G shown in FIG. 10. Rollers 58 grip the line 10 and the frame 50 moves downwardly back to the hand insertion station H shown in FIG. 11 where a glove is opened in the same manner as described above, ready for a user to insert his hand into the apparatus to locate the glove on the user's hand. Once this happens, and the user's hand is removed from the apparatus the sequence starts again and the frame 50 is driven upwardly so that the rollers rotate until the line is then gripped and the frame 50 moved downwardly to draw the line 10 from the roll 15 and open a fresh glove in the apparatus when the frame 50 returns to the station H as shown in FIG. 11. Thus, the insertion of a user's hand into the apparatus and removal of the hand and glove provides the signal to operate the apparatus to open another glove ready for a user to place his hand into the glove. Thus, after a glove is removed from the line by a user a fresh glove is delivered to the hand insertion station H shown in FIG. 11 ready for another hand to be inserted into a glove.

It will be noted from the above that the rollers 58 only rotate during the upward movement of the frame 50. During the lowering of the frame 50 the rollers 58 grip the line of gloves 10 and do not rotate thereby drawing further gloves from the roll 15.

In order to facilitate rotation of the rollers 58 during movement of the indexing device 48 a driver is provided to rotate the rollers 58 during movement to the station G but which will allow the rollers to be locked against rotation during movement of the indexing device 48 back to the hand insertion station H. In one embodiment the driver comprises a motor 69 which has a clutch or ratchet mechanism so the motor can rotate the rollers during movement to the gripping station G but allow the rollers to remain locked against rotation during movement back to the hand insertion station H.

The motor 69 (see FIG. 9) is provided on the shaft 62 to rotate the roller 58 on that shaft with the rotation being imparted to the other roller by meshing engagement of the gears 59.

Figure 17:
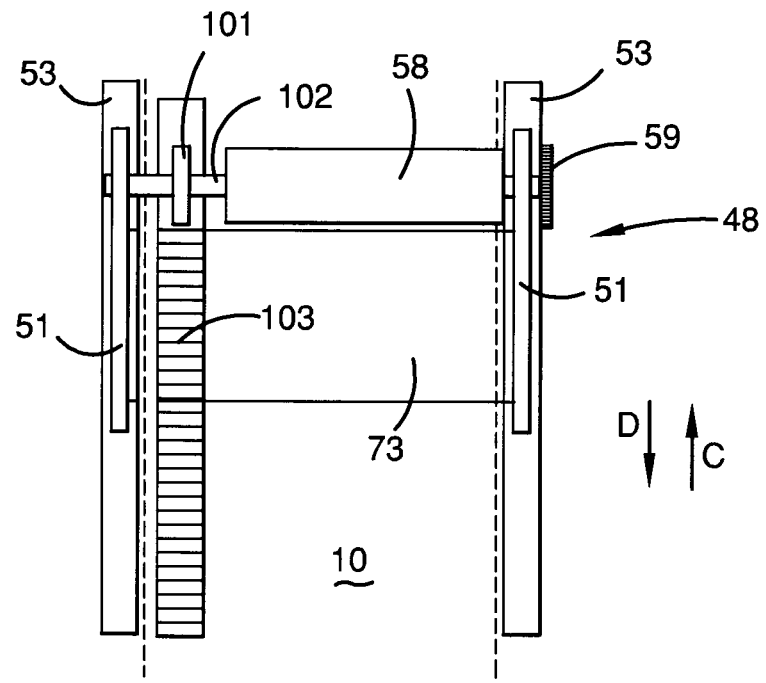
FIG. 17 is a schematic view of part of the apparatus of FIG. 9.

In another embodiment as shown in FIG. 17 the driver comprises a gear 101 mounted on shaft 102 on which one of the rollers 58 is provided. The gear 101 meshes with a rack 103 fixed to housing 55 (shown in FIG. 16). The gear 101 is mounted to the shaft 102 via a ratchet, clutch or the like so that when the indexing device 48 is moved upwardly towards the gripping station G in the direction of arrow C in FIG. 17 the engagement of the gear 101 and the rack 103 causes rotation of the gear 101 and therefore the shaft 102 and roller 58. Rotation is imparted to the other roller 58 by the gears 59. Thus, the rollers 58 easily roll up the line 10 of the gloves 11. During movement back towards the hand insertion station in the direction of arrow D the ratchet or clutch associated with the gear 101 allows the gear 101 to rotate freely on the shaft 102 so no rotation is imparted to the rollers 58 and the rollers remain in the locked position with the rib 70 located in the groove 71 as previously explained.

The provision of the gear 101 also provides the additional advantage in that it synchronises the upward movement of the indexing device 48 in the direction of arrow C with the rotation of the rollers 58 so the rollers undergo one full revolution during complete movement of the indexing device from the hand insertion station H to the gripping station G.

It will be appreciated from the previous description and drawings that the rollers 58 extend only part the distance of the space between the frame members 51 and therefore adequate space is provided for the motor 69 or the gear 101 and rack 103.

Figure 12:
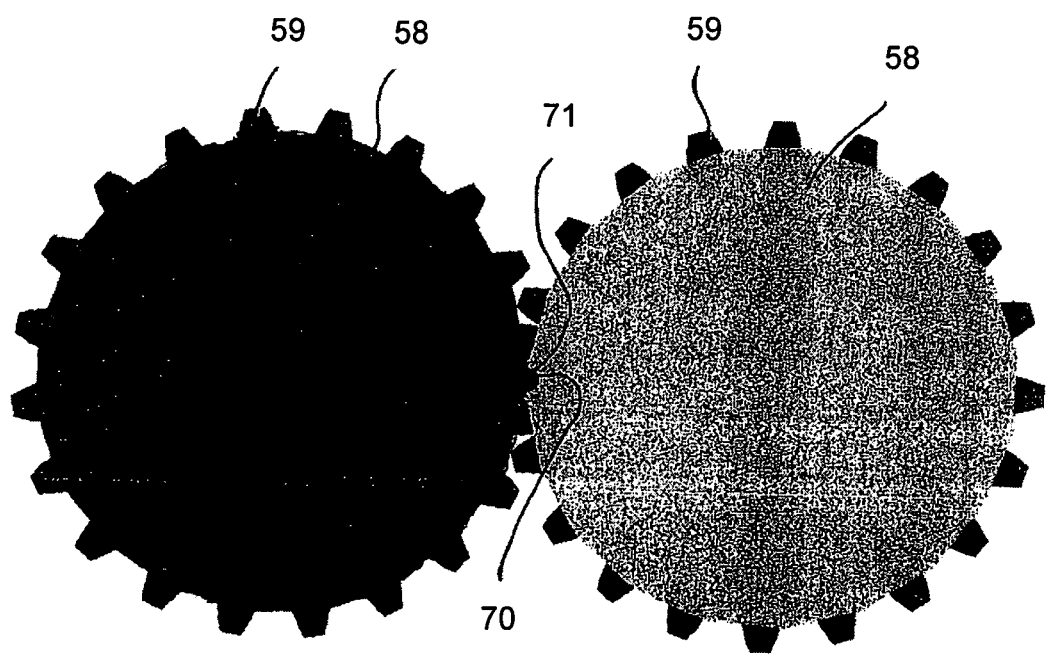
FIG. 12 is a detailed view of a roller and gear assembly using the preferred embodiment of the invention.

As shown in FIG. 12 the rollers 58 are configured to grip the line 10 when the frame 50 is in the upper position shown in FIG. 9. To achieve this one of the rollers 58 (i.e. the left roller in FIG. 12) is provided with a longitudinal rib 70 and the other roller 58 is provided with a longitudinal groove 71. When the frame 50 is the upper position at gripper station G the rib 70 locates in the groove 71 therefore jamming the line 10 between the rib 70 and groove 71 so that the rollers 58 firmly hold the line 10. When the frame 50 is moved downwardly the rollers 58 therefore firmly grip the line 10 and the line 10 is drawn off the roll 15 with downward movement of the frame 50. When the frame 50 is moved upwardly, the rollers 58 are able to rotate so the rib 70 moves out of the groove 71 so that the rollers 58 can effectively roll up the line 10 for one full rotation of the rollers 58 until the rib 70 relocates in groove 71 to again grip the line 10.

Figure 13:
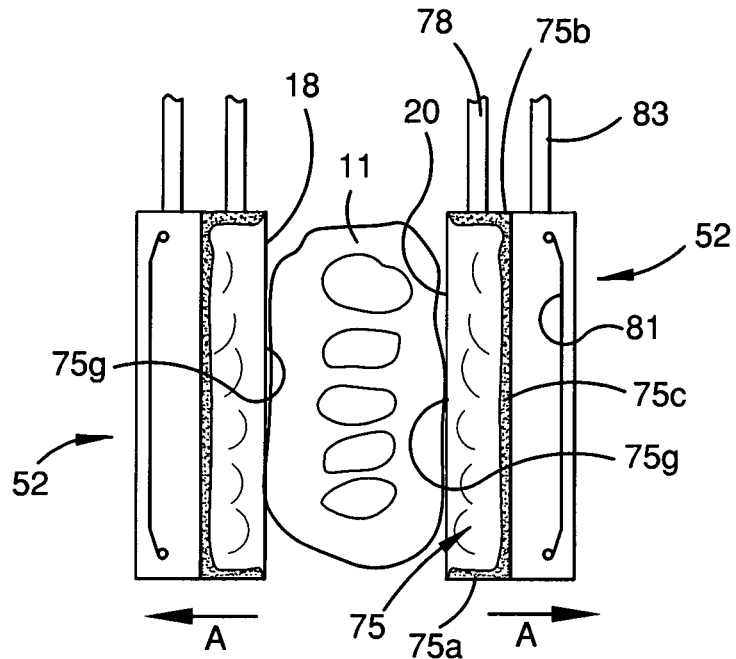
FIG. 13 is a schematic view of part of the apparatus of FIG. 9.
Figure 14:
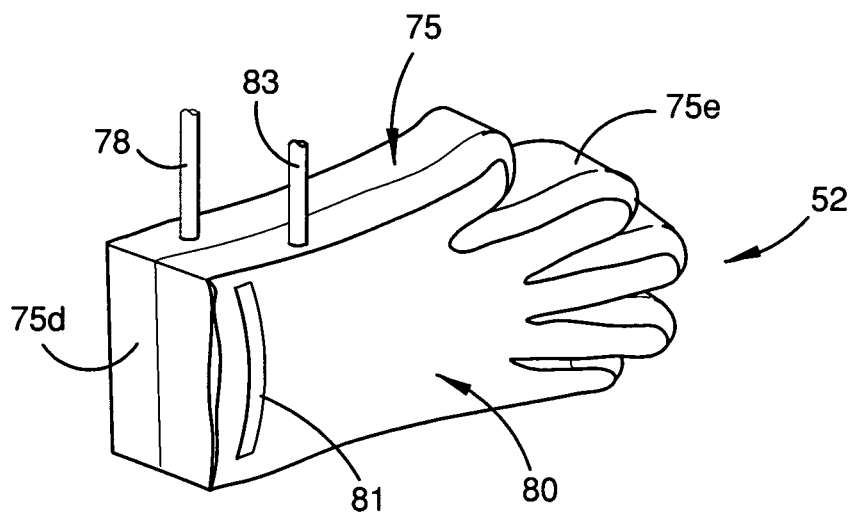
FIG. 14 is a perspective view of part of the apparatus shown in FIG. 13.
Figure 15:
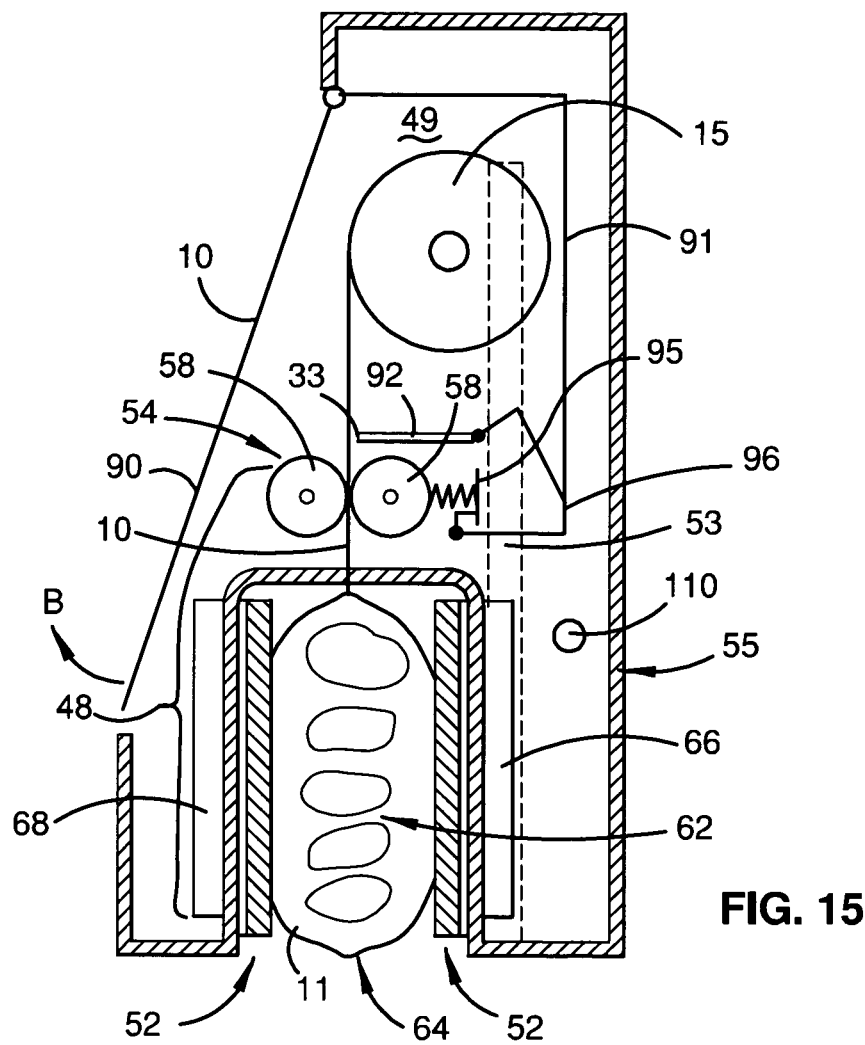
FIG. 15 is a schematic front view of an apparatus according to FIG. 9.
Figure 16:
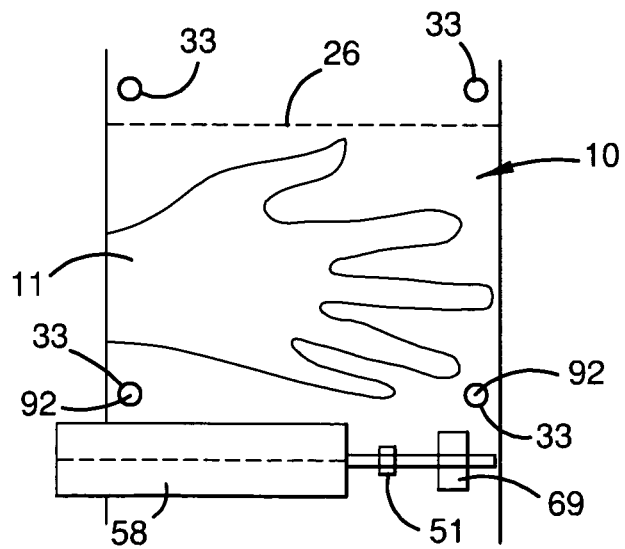
FIG. 16 is a side view of part of the apparatus of FIG. 15.

FIGS. 13 and 14 show in more detail the devices 52 according to a first embodiment for opening a glove 11. The devices 52 are supported on plates 73 which form part of the frame 50 and extend between the frame members 51. The plate 73 and the frame members 51 therefore form partial enclosures for securely supporting the devices 52.

Each device 52 is identical and therefore only one will be described in detail in FIGS. 13 and 14. Each device 52 comprises a open cell foam block 75 which is in the general shape of the glove 11 except that the fingers are somewhat shorter than the fingers of the glove 11. The block 75 has a layer of lacquer or other sealant applied to edges 75a, 75b and rear surface 75c. End edges 75d and the edges which define the finger portions 75e also have the lacquer or sealant coating applied to them. A vacuum tube 78 is connected with the block 75 and in turn connects with one of the pressure pumps 60. A bladder 80 is connected on the outside of the block 75 against surface 75c and again has the same general shape as the block 75. The bladder includes a plastic strip 81 within the bladder which acts as a spring as will be described in more detail hereinafter. A supply tube 83 is connected to the bladder 80 and also to the other of the pumps 60. Thus, one of the pumps 60 enables vacuum to be applied to the two devices 52 (namely the blocks 75 of the two devices 52) and the other pump 60 supplies pressure to the two bladders 80 of the devices 52.

In order to open the glove 11 air is pumped from one of the pressure pumps 60 into the bladders 80 to cause the bladders 80 to expand. The spring generally holds the bladders 81 against spherical expansion of the bladders 80 and therefore when the bladders expand they push against the blocks 75 to push the blocks 75 into engagement with a closed glove 11 as is best shown in FIG. 10. Thus, the open porous faces 75g of the blocks 75, which do not have lacquer or sealant applied to them, are pushed into gentle contact with the layers 18 and 20 which make up the glove 11. Vacuum is then drawn by the other pump 60 through the tube 78 and through the open cellular structure of the foam block 75 so that the webs 18 and 20 are sucked against the surface of 75g of the blocks 75. At the same time, pressure is released from the bladders 80 causing the bladders to return to their generally flat deflated configuration shown in FIG. 14 pulling the block 75 with them in the direction of arrows A in FIG. 13. This thereby cause layers 18 and 20 to separate and open the glove 11 sufficient for a person to insert his or her hand into the glove 11 through open door 62 of the housing 55.

Figure 18:
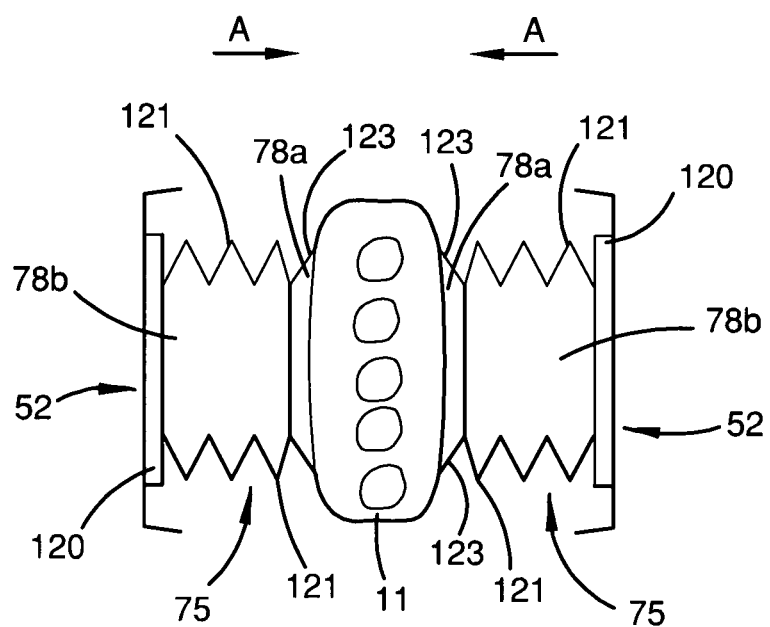
FIG. 18 is a schematic view of a part of the apparatus according to another embodiment of the invention.
Figure 19:
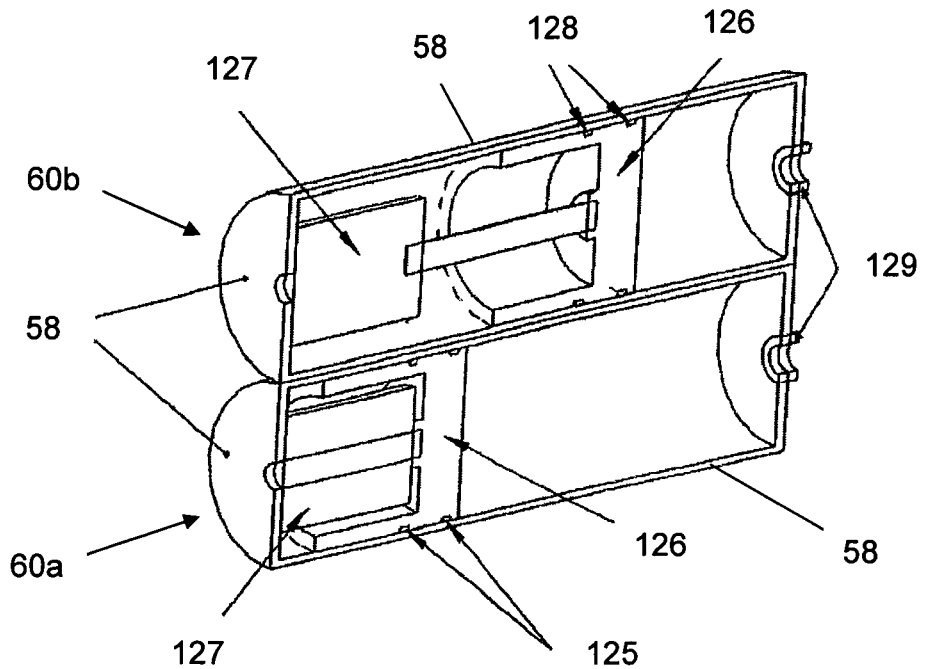
FIG. 19 is a cross-sectional view of another part of the apparatus according to an embodiment of the invention.
Figure 20:
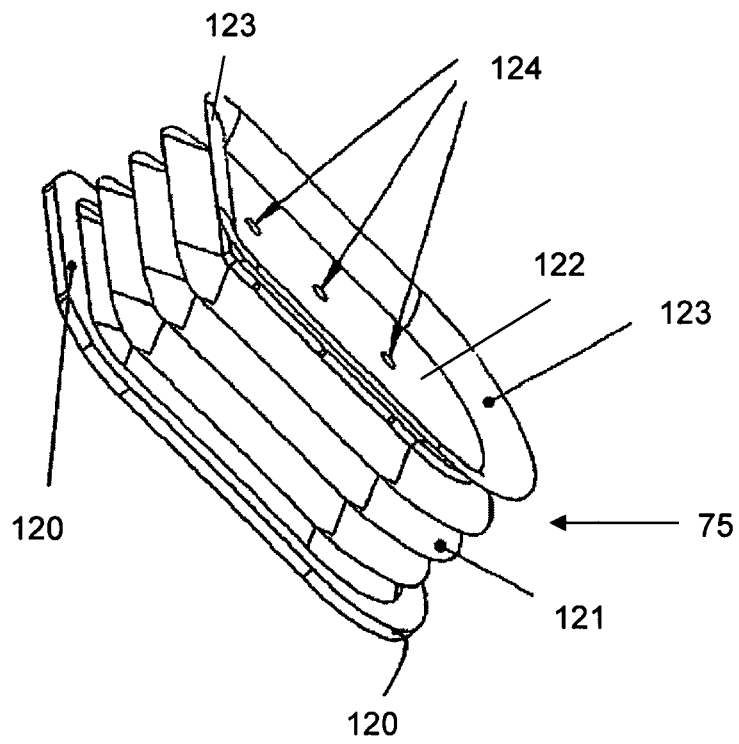
FIG. 20 is a perspective view of a section of the part of the apparatus shown in FIG. 18.
Figure 21:
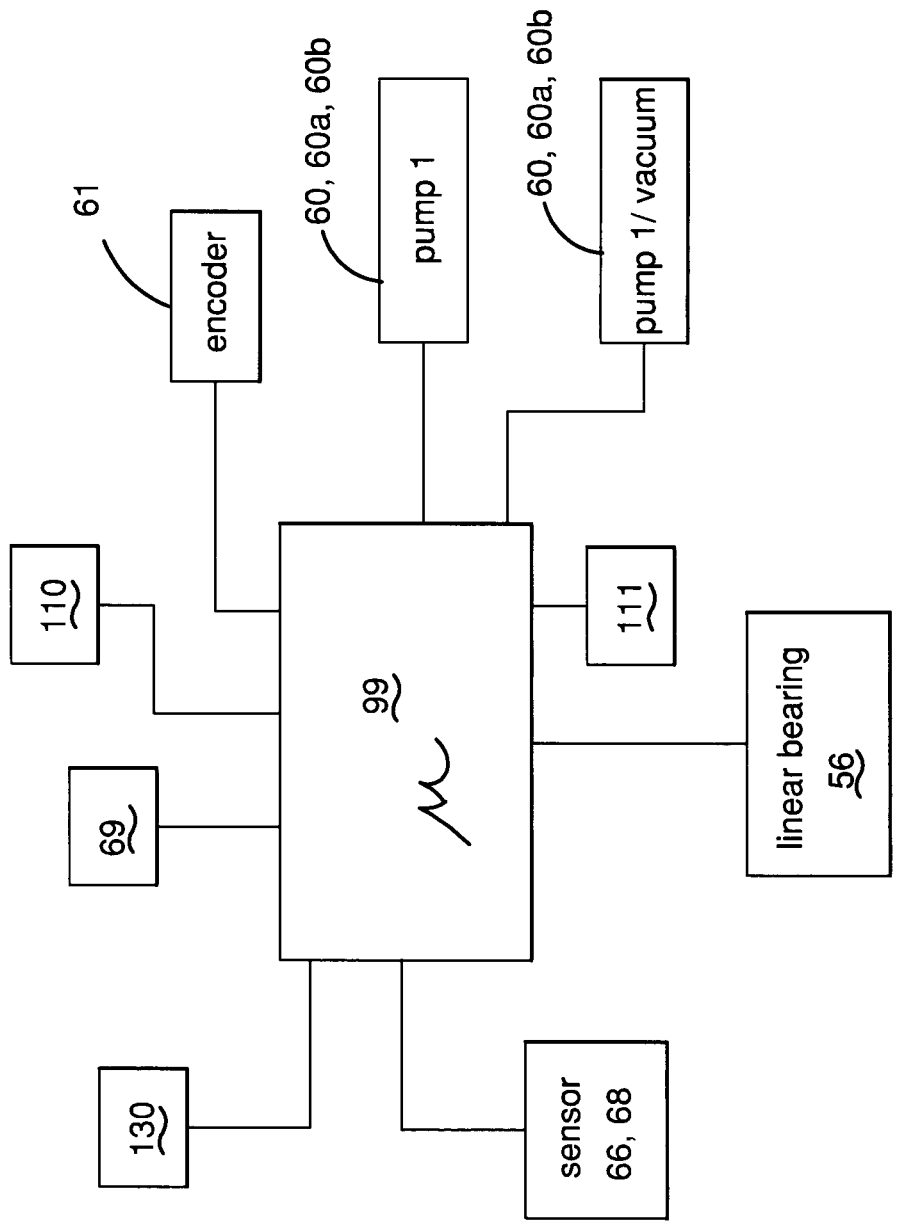
FIG. 21 is a schematic diagram of a control system used in the embodiment of the invention.

FIGS. 18 to 20 show the devices 52 of an alternative embodiment for opening the glove 11. The devices are supported on plates 73, best seen in FIG. 17, which form part of the frame 50 and extend between the frame members 51 shown in FIGS. 9 to 15. The plate 73 and the frame members 51 therefore form partial enclosures for securely supporting the devices 52.

Each device 52 is the same and therefore only one will be described in detail. Each device 52 comprises a bellows 75 having a clamping ring 120 for securing the bellows 75 to the plate 73, a flexible and inflatable diaphragm 121 having a side wall comprising a series of the folds and an engagement face 122 that approximates the size of the palm region of the glove 11. Arranged about the perimeter of the engagement face 122 is a vacuum sealing lip 123 and central of the engagement face 122 are three suction holes 124 that are each connected to a vacuum source 60a via a manifold and tubing 78a. The diaphragm 121 of the bellows 75 is connected to an air delivery system comprising an air displacement pump 60b. FIG. 19 shows an embodiment in which the vacuum source 60a and air displacement pump 60b are in the form of piston and cylinder assemblies located within rollers 58 for guiding the line 10 of gloves 11. The inside of walls of the rollers 58 form the cylinder and a piston 126 having vacuum seals 125 or pump seals 128 and each is driven inside the cylinders by a solenoid controlled linear actuator 127. The end wall of each roller 58 is equipped with a rotary air coupling for coupling to air supply tubing 78a, 78b. In the case of the vacuum source, tubing 78a connects the cylinder of the vacuum source to the holes 124 in the face of the engagement face 122 via a manifold. In the case of the air displacement pump, tubing 78b connects the cylinder to the inside of the diaphragm 121.

In order to open the glove 11 the liner actuator 127 of the air pump 60b is operated to move the piston to the distal end of the roller 58 and thereby expand the bellows 75 in the direction of arrows A in FIG. 18 until the lip sealing formation 123 engages the palm region of a glove 11 at the insertion station H. Pressure release valves or flow regulates may be incorporated into the air pump 60b or the tubing 78b to limit over pressurisation or under pressurisation of the bellows 75 as deemed necessary. With the bellows 75 expanded and lip formations 123 contacting opposite layers or sides of the glove 11, the vacuum source 60a is operated to retain the each respective layer of the glove 11 to the bellows 75. The linear actuator 127 of the vacuum 60a is operated by moving the piston toward the proximal end of the roller 58 in FIG. 19. Once the formation of an adequate vacuum has been established to retain the layers of the glove 11 to the engagement face 122, the linear actuator 127 of the air displacement pump 60b drives the piston from the distal end to proximal end of the cylinder, thereby deflating the bellows 75 and simultaneously opening the glove ready for hand insertion. The adequacy or inadequacy of inflation and deflation of the bellows 75 can be monitored by way of the pressure release valves or flow regulators. Similarly, the adequacy or inadequacy of the vacuum for retaining the layers of the glove 11 to the engagement face 122 of the bellows 75 can be monitored using suitable regulators.

Irrespective of whether the devices 52 for opening the glove are in the form of the embodiment shown in FIGS. 13 and 14, or the alternative embodiment shown in FIGS. 18 and 20, insertion of a hand into the glove blocks the light from the emitter array 66 to the detector array 68 indicating a hand has been placed in the glove. As previously explained, the user then pulls his or her hand downwardly through open bottom 64 to tear the glove 11 along perforated line 26 with the glove on the user's hand. As the user's hand is removed from the apparatus light is again detected by the array 68 providing a signal for the frame 50 to be driven upwardly to again grip the line and move downwardly with another glove being opened as the frame 50 moves downwardly so that a user can insert his or her other hand into the next glove if desired. Otherwise, the glove is simply held in the open configuration in the device awaiting for the next hand to be inserted into that glove and for that glove to be torn from the line 10 before the sequence repeats to bring another glove to the hand insertion station H.

Vacuum may be applied to hold a glove in the open position at the insertion station H for a predetermined time interval after which the vacuum is shut off. Thus, if a glove is not required for some time, the glove merely remains in a static position at the hand insertion station. A sensor (not shown) may be provided to activate the glove opening device to open the glove again when a hand is inserted into the apparatus.

In another embodiment the cycle of retrieving a new glove and opening a new glove may be commenced by a start button 110 (see FIG. 15) and the sequence of operation may be that when the button 110 is pushed the indexing device 48 moves upwardly as previously explained to grip the line 10 and then moves back to the hand insertion station with the glove being opened as previously explained so the user can insert his or her hand into the glove. When another glove is required the button 110 is again pushed so the sequence repeats itself. This prevents the need to hold vacuum at the opening devices 52 for a great length of time.

As is best shown in FIG. 15, the housing 55 is provided with a door 90 which can be opened in the direction of arrow B to enable a new roll 15 to be loaded into the apparatus. To load a new roll the door 90 is opened and the remnants of the old roll 15 removed. A new roll is located in place in the apparatus. When the door 90 is opened, a mechanical linkage schematically shown at 91 causes two pins 92 to be driven forward. The locating holes 33 in one of the panels 25 of line 10 are located on the pins 92 so the pins 92 project through the holes 33. This correctly registers the roll relative to the rollers 58 and part of the line 10 is located between the rollers 58. To facilitate location of the line 10 between the rollers 58 one of the rollers 58 is mounted on a spring tensioning device 95 which, when the door 90 is opened, draws the respective roller 58 away from the other roller 58 to provide a space for the line 10 to be easily inserted between the rollers. Again a mechanical link 96 (schematically shown) may be used to achieve this. When the door 10 is closed the pins 92 are retracted out of the holes 33 away from the line 10 and the roller 58 is again spring biased against the other roller 58 with the line 10 between the rollers 58.

When the door 90 is closed the apparatus can be operated to locate a glove at the hand insertion station with the glove open ready for use by a user.

FIG. 18 is a schematic block diagram of the control system for controlling the apparatus. A processor 99 is provided which receives signals from the encoder 61 to monitor the position of the rollers 58 relative to one another and to stop movement of linear bearings 56 when the rollers 58 have rotated one full revolution. Photo detector array 66 and 68 also provide signals to the processor 99 to indicate location removal of a user's hand to drive the linear bearings 56 to move the indexing device 48 upwardly and then back down to the hand insertion station H and at the same time operate the pumps and/or vacuum source to apply pressure and vacuum to the devices 52 to grip the glove and open the glove. In the event that the pressure release values or air regulators detect that inadequate or excessive air flow is created by pumps 60, 60a or 60b, causing malfunction of the devices 52, the processor 99 can activate an alarm 130 signalling that the apparatus requires maintenance or servicing.

The processor 99 also receives a signal when the button 100 is pressed, should the button be provided, to commence the glove retrieval and opening sequence, and a signal from timer 111 for shutting off the vacuum to the opening devices 52 after a predetermined time period.

If a motor 69 is provided for facilitating rotation of the rollers 58 during upward movement of the frame 50 the processor 99 can also control the motor 69 to drive the roller 68 during movement of the indexing device 48 from station H to station G until one full rotation of the rollers 58 has occurred.

Other sensors may also be included in the apparatus to detect the location of the line 10 and is indexing through the apparatus from the roll 15 to the hand insertion station. Further markings or other indicia may be provided on the line 10 to facilitate detection of the line 10 by the other sensors.

In order to provide additional rigidity to the line 10 of the gloves 11, the layers 18 and 20 may be provided with additional rigidity such as by forming a double heat seal about the periphery of the glove 11 or providing a thickened heat seal bead along the line 11. The additional rigidity will assist in ensuring that the line 10 moves vertically downwardly and does not tend to wrap around the rollers 58 during indexing of the line 10 through the apparatus.

Since modifications within the spirit and scope of the invention may readily be effected by persons skilled within the art, it is to be understood that this invention is not limited to the particular embodiment described by way of example hereinabove.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The claims defining the invention are as follows:

1. An apparatus for enabling hygienic location of a glove on a hand, comprising:
 a storage for storing a package of disposable gloves, the package being a continuous line of gloves wherein consecutive ones of the gloves are connected together by a respective frangible connection which is breakable to separate one of the gloves from the line;
 an indexing device for moving the gloves from the storage to a hand insertion station of the apparatus; and a glove opening device for opening a glove of the package so a user can insert his or her hand into the glove at the hand insertion station;

wherein the indexing device includes a gripping device comprising a pair of opposed rollers for gripping the line of gloves between the rollers, the indexing device being arranged for movement between the hand insertion station and a line gripping station of the apparatus so that the rollers can move relative to the line of gloves between the hand insertion station and the gripping station, and can grip the line of gloves at the line gripping station so the line of gloves is drawn with the rollers upon return movement of the indexing device from the gripping station to the hand insertion station, and wherein the glove opening device is arranged to move between the hand insertion station and the line gripping station with the indexing device.

2. The apparatus according to claim 1, wherein the package of gloves is a roll of gloves and the storage is a compartment for storing the roll of gloves.

3. The apparatus according to claim 1, wherein the gloves in the line have a first layer and a second layer and the glove opening device comprises a gripper for gripping at least one of the layers, and a gripper moving element for moving the gripper and the at least one of the layers relative to the other layer to open the glove.

4. The apparatus according to claim 3, wherein the glove is gripped and opened during movement of the gripping device between the gripping station and the hand insertion station.

5. The apparatus according to claim 1, wherein the gripper comprises an inflatable assembly and a sealing formation having one or more than one suction points, wherein upon inflation of the inflatable assembly, at least one of the suctions points of the sealing formation is located against at least one of the layers, and upon deflation of the inflatable assembly, the layer is drawn away from the other layer to thereby open the glove.

6. The apparatus according to claim 5, wherein the inflatable assembly comprises a bellows.

7. The apparatus according to claims claim 5, wherein the rate of inflation or deflation of the inflatable assembly is controlled by a piston and cylinder that supplies air into, or draws air from, the inflatable assembly, and suction of the suctions points is controlled by a separate piston and cylinder.

8. The apparatus according to claim 7, wherein the piston and cylinder assemblies are operable by a linear actuator controlled by a solenoid.

9. The apparatus according to claim 1, wherein the indexing device further comprises a gear attached to each said roller, the gears meshing together so the rollers are able to rotate in unison but in opposite directions, the rollers having a groove and rib so that when the groove of one roller engages with the rib of the other roller the line of gloves is gripped between the rollers, and so that upon the return movement of the indexing device from the gripping station to the hand insertion station the line is drawn off the package, and upon movement of the indexing device from the hand insertion station to the gripping station the rollers rotate relative to the line during movement of the indexing device until the groove and rib re-engage to thereby grip the line between the rollers.

10. The apparatus according to claim 9, wherein a driver is provided to rotate the rollers only during movement of the gripping device from the hand insertion station to the gripping station.

11. The apparatus according to claim 1, further including a sensor for sensing the insertion of a user's hand into the glove at the hand insertion station, and then removal of the glove from the line at the hand insertion station, to thereby activate the indexing device to cause the indexing device to move from the hand insertion station-, to the gripping station and back to the hand insertion station so a new glove is open at the hand insertion station ready for insertion of a user's hand.

12. The apparatus according to claim 1, further including locating elements for engaging the line when a new package is located in the apparatus to correctly register the line in the apparatus.

13. The apparatus according to claim 12, wherein the line has holes and the locating elements comprise pins for passing through the holes when the package is loaded into the apparatus, and for withdrawal from the holes after the package is loaded in the apparatus.

14. The apparatus according to claim 13, wherein the pins are driven between a locating position where they can pass through the holes and a retracted position away from the line, by opening and closing movement of a door of the apparatus to provide access to the storage of the apparatus.

15. The apparatus according to claim 1, wherein the glove opening device comprises at least one inflatable assembly having openings therein through which air can flow, and at least one air supply and vacuum system for supplying air to the inflatable assembly to inflate and thereby locate the openings of the assembly in a position adjacent the glove, for drawing a vacuum through the assembly so a portion of the glove is drawn against the assembly, and for deflating the assembly so the assembly moves a portion of the glove away from another portion of the glove to open the glove to enable the user to insert his or her hand into the glove at the hand insertion station.

16. An apparatus for enabling hygienic location of a glove on a hand, comprising:

a housing having a front opening and a bottom opening which provide access to a hand insertion station;

a storage for storing a package of a continuous line of disposable gloves in which consecutive ones of the gloves are connected together by a respective frangible connection between a cuff portion of the gloves and a fingertip portion of the gloves and which is breakable to separate one of the gloves from the line, the storage being for storage of the package so the gloves are presented at the hand insertion station in an orientation so that the frangible connection is substantially horizontal, and with the cuff portion of the gloves facing the front opening;

a glove indexing device for moving a glove from the storage to the hand insertion station; and a glove opening device for opening the glove so a user can insert his or her hand into the glove through the cuff portion;

wherein the indexing device includes a gripping device comprising a pair of opposed rollers for gripping the line of gloves between the rollers, the indexing device being arranged for movement between the hand insertion station and a line gripping station of the apparatus so that the rollers can move relative to the line of gloves between the hand insertion station and the gripping station, and can grip the line of gloves at the line gripping station so the line of gloves is drawn with the rollers upon return movement of the rollers from the gripping station to the hand insertion station, and the glove opening device is arranged to move between the hand insertion station and the gripping station with the indexing device; and wherein to locate the glove on the hand and remove the glove from the apparatus, a user inserts his or her hand through the front opening of the housing into the glove opened by the glove opening device and then moves his or her hand with the glove on his or her hand downwardly through the bottom opening of the housing.

17. A package of disposable gloves in combination with a glove applying apparatus for enabling hygienic location of a glove of the package on the hand of a user, the glove applying apparatus comprising:
a storage for storing the package of disposable gloves, the package being a continuous line of gloves wherein consecutive ones of the gloves are connected together by a representative frangible connection which is breakable to separate one of the gloves from the line;
an indexing device for moving the gloves from the storage to a hand insertion station of the apparatus; and
a glove opening device for opening respective gloves of the package so the user can insert his or her hand into an opened said glove at the hand insertion station;
wherein the indexing device includes a gripping device comprising a pair of opposed rollers for gripping the line of gloves between the rollers, the indexing device being arranged for movement between the hand insertion station and a line gripping station of the apparatus so that the rollers can move relative to the line of gloves between the hand insertion station and the gripping station, and can grip the line of gloves at the line gripping station so the line of gloves is drawn with the rollers upon return movement of the indexing device from the gripping station to the hand insertion station, and wherein the glove opening device is arranged to move between the hand insertion station and the gripping station with the indexing device.

18. A package of disposable gloves according to claim 17, wherein each glove of the package has a glove edge transverse to the frangible connection, the glove edge forming an open cuff of each glove, and wherein each glove is formed from two layers which are joined together by a join to define the glove.

19. A package of disposable gloves according to claim 17, wherein the gloves are formed in glove panels with each panel being connected to an adjacent panel by the frangible connection, the join comprising a heat seal in each panel defining the shape of the glove.

20. A package of disposable gloves according to claim 19, wherein each panel is a rectangular panel and has webs outwardly of the join.

21. A package of disposable gloves according to claim 20, wherein each glove has defined fingers and the webs are formed between the fingers and cuts are formed through the webs between the fingers to separate the fingers.

22. A package of disposable gloves according to claim 21, wherein the glove has fingers and the join of the glove which defines the fingers forms the periphery of the panel at the fingers.

23. The package of disposable gloves according to claim 17, wherein the package is in the form of a roll of gloves.

24. An apparatus for enabling hygienic location of a glove on a hand, comprising:
a storage for storing a package of disposable gloves, the package being a continuous line of gloves wherein consecutive ones of the gloves are connected together by a respective frangible connection which is breakable to separate one of the gloves from the line;
an indexing device for moving the gloves from the storage to a hand insertion station; and
a glove opening device comprising at least one inflatable assembly having openings therein through which air can flow, and at least one air supply and vacuum system for supplying air to the inflatable assembly to inflate and thereby locate openings of the assembly in a position adjacent the glove, for drawing a vacuum through the assembly so a portion of the glove is drawn against the assembly, and for deflating the assembly so the assembly moves a portion of the glove away from another portion of the glove to open the glove to enable a user to insert his or her hand into the glove at the hand insertion station; and
wherein the indexing device includes a gripping device comprising a pair of opposed roller for gripping the line of gloves between the rollers, the indexing device being arranged for movement between the hand insertion station and a line gripping station of the apparatus so that the rollers can move relative to the line of gloves between the hand insertion station and the gripping station, and can grip the line of gloves at the line gripping station so the line of gloves is drawn with the rollers upon return movement of the indexing device from the gripping station to the hand insertion station, and wherein the glove opening device is arranged to move between the hand insertion station and the line gripping station with the indexing device.

25. A method of hygienically locating a glove on a user's hand, comprising:
providing an apparatus loaded with a package of gloves in the form of a continuous line, the gloves being arranged one after another in the line wherein consecutive ones of the gloves are connected together by a respective frangible connection, the frangible connection being breakable to separate one of the gloves from the line, and the apparatus including an indexing device, and a glove opening device for opening respective of the gloves, wherein the indexing device includes a gripping device comprising a pair of opposed rollers for gripping the line of gloves between the rollers, the indexing device being arranged for movement between a hand insertion station and a line gripping station of the apparatus so that the rollers can move relative to the line of gloves between the hand insertion station and the gripping station, and can grip the line of gloves at the line gripping station so the line of gloves is drawn with the rollers upon return movement of the indexing device from the gripping station to the hand insertion station, and wherein the glove opening device is arranged to move between the hand insertion station and the line gripping station with the indexing device;
mechanically locating a said glove at a hand insertion location of the apparatus with said return movement of the indexing device, the glove at the hand insertion location being opened by the glove opening device; and
the user inserting a hand in the opened glove, the glove being removed from the line of gloves with removal of the hand from the hand insertion location of the apparatus.

26. The method according to claim 25, wherein the glove has a first layer defining the back of the glove and a second layer defining the palm of the glove, and opening the glove involves an apparatus moving the first and second layers apart to enable a person to insert his/her hand through the cuff into the glove.

* * * * *